(12) United States Patent
Pruehs et al.

(10) Patent No.: US 8,779,160 B2
(45) Date of Patent: Jul. 15, 2014

(54) PROCESS FOR THE PREPARATION OF (1R,4R)-6'-FLUORO-(N,N-DIMETHYL- AND N-METHYL)-4-PHENYL-4',9'-DIHYDRO-3'H-SPIRO[CYCLOHEXANE-1,1'-PYRANO-[3,4,B]INDOL]-4-AMINE

(71) Applicant: Gruenenthal GmbH, Aachen (DE)

(72) Inventors: Stefan Pruehs, Neuss (DE); Carsten Griebel, Aachen (DE); Wolfgang Hell, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 13/711,455

(22) Filed: Dec. 11, 2012

(65) Prior Publication Data

US 2013/0150590 A1 Jun. 13, 2013

Related U.S. Application Data

(60) Provisional application No. 61/569,491, filed on Dec. 12, 2011.

(30) Foreign Application Priority Data

Dec. 12, 2011 (EP) .................................... 11009765

(51) Int. Cl.
C07D 491/107 (2006.01)
A61K 31/407 (2006.01)
(52) U.S. Cl.
CPC ........... *C07D 491/107* (2013.01); *A61K 31/407* (2013.01)
USPC ......................................................... 548/407
(58) Field of Classification Search
CPC .......................... C07D 491/107; A61K 31/407
USPC ......................................................... 548/407
See application file for complete search history.

(56) References Cited

U.S. PATENT DOCUMENTS

| 7,799,931 | B2 * | 9/2010 | Hinze et al. | 548/421 |
| 7,960,404 | B2 * | 6/2011 | Schunk et al. | 514/278 |
| 2011/0015220 | A1 | 1/2011 | Linz et al. | |
| 2011/0319440 | A1 | 12/2011 | Hinze et al. | |
| 2013/0123324 | A1 * | 5/2013 | Gruss et al. | 514/409 |

FOREIGN PATENT DOCUMENTS

| WO | WO 2004/043967 A1 | 5/2004 |
| WO | WO 2008/040481 A1 | 4/2008 |

OTHER PUBLICATIONS

Schaefgen et al. "Ionization Constants of Butylamine, Piperidine and Triethylamine in Methanol" J. Am. Chem. Soc. 1944, 66, 1847-49.*
Molchanov et al. "Corrosion of Silicate Glasses by Alkaline Solutions" B. Acad. Sci. USSR, 1958, 7, 893-897.*
Reutzel-Edens et al., "Physical Characterization of Hygroscopicity in Pharmaceutical Solids", Polymorphism in the Pharmaceutical Industry, 2006, pp. 235-242 (ten (10) sheets).
Extended European Search Report dated Mar. 23, 2012 (five (5) sheets).
International Search Report including Written Opinion (PCT/ISA/237) dated Jan. 31, 2013 {Nine (9) Pages}.
Chou, Shan-Yen, "A Novel Substitution Reaction of Tetrahydropyrano[3,4-b]Indole Derivative—Chain Extension and Structural Correlation Study", Heterocycles, Mar. 2003, pp. 1095-1110, vol. 60, No. 5.
Zott, Matthias et al., "Tricyclic Benzomorphan Analogues by Intramolecular Oxa-Pictet-Spengler Reaction", Tetrahedron: Asymmetry, 1993, pp. 2307-2310, vol. 4, No. 11, Pergamon Press Ltd., Great Britain.
Ravin, L. PhD., "Preformulation", Remington Chapter 76, pp. 1409-1423, 1985 (fifteen (15) sheets).
DiSanto, A., "Bioavailability and Bioequivalency Testing", Remington Chapter 77, pp. 1424-1431, 1985 (eight (8) sheets).
Knevel, A. PhD., "Separation", Remington Chapter 78, pp. 1432-1442, 1985 (eleven (11) sheets).
Phillips, G Briggs, PhD., "Sterilization", Remington Chapter 79, pp. 1443-1454, 1985 (twelve (12) sheets).
Siegel, F. PhD., "Tonicity, Osmoticity, Osmolality and Osmolarity", Remington Chapter 80, pp. 1455-1472, 1985 (eighteen (18) sheets).
Giles et al., "Plastic Packaging Materials", Remington Chapter 81, pp. 1473-1477, 1985 (five (5) sheets).
Lintner, C. PhD., "Stability of Pharmaceutical Products", Remington Chapter 82, pp. 1478-1486, 1985 (nine (9) sheets).
Erskine, C., Jr., "Quality Assurance and Control" Remington Chapter 83, pp. 1487-1491, 1985 (five (5) sheets).
Nairn, J.G. PhD., "Solutions, Emulsions, Suspensions and Extractives", Remington Chapter 84, pp. 1492-1517, 1985 (twenty-six (26) sheets).
Avis, K. DSc., "Parenteral Preparations", Remington Chapter 85, pp. 1518-1541, 1985 (twenty-four (24) sheets).
Turco et al., "Intravenous Admixtures", Remington Chapter 86, pp. 1542-1552, 1985 (eleven (11) sheets).
Mullins, J. PhD., "Ophthalmic Preparations", Remington Chapter 87, pp. 1553-1566, 1985 (fourteen (14) sheets).
Block, L. PhD., "Medicated Applications", Remington Chapter 88, pp. 1567-1584, 1985 (eighteen (18) sheets).
Rippie, E. PhD., "Powders", Remington Chapter 89, pp. 1585-1602 (eighteen, 1985 (18) sheets).
King et al., "Oral Solid Dosage Forms", Remington Chapter 90, pp. 1603-1632, 1985 (thirty (30) sheets).
Porter, S. PhD., "Coating of Pharmaceutical Dosage Forms", Remington Chapter 91, pp. 1633-1643, 1985 (eleven (11) sheets).
Longer et al., "Sustained-Release Drug Delivery Systems", Remington Chapter 92, pp. 1644-1661, 1985 (eighteen (18) sheets).
Sclarra et al., "Aerosols", Remington Chapter 93 , 1985, pp. 1662-1677, (sixteen (16) sheets).

\* cited by examiner

*Primary Examiner* — Samantha Shterengarts
*Assistant Examiner* — Amanda L Aguirre
(74) *Attorney, Agent, or Firm* — Crowell & Moring LLP

(57) ABSTRACT

A process for the preparation of (1r,4r)-6'-fluoro-N,N-dimethyl-4-phenyl-4',9'-dihydro-3'H-spiro[cyclohexane-1,1'-pyrano[3,4b]indol]-4-amine and (1r,4r)-6'-fluoro-N-methyl-4-phenyl-4',9'-dihydro-3'H-spiro[cyclohexane-1,1'-pyrano[3,4b]-indol]-4-amine or physiologically acceptable acid addition salts thereof.

15 Claims, No Drawings

PROCESS FOR THE PREPARATION OF (1R,4R)-6'-FLUORO-(N,N-DIMETHYL- AND N-METHYL)-4-PHENYL-4',9'-DIHYDRO-3'H-SPIRO[CYCLOHEXANE-1,1'-PYRANO-[3,4,B]INDOL]-4-AMINE

CROSS REFERENCE TO RELATED APPLICATIONS

This application claims priority based on U.S. provisional patent application No. 61/569,491, filed Dec. 12, 2011, the entire disclosure of which is incorporated herein by reference. Priority is also claimed based on European patent application no. EP 11 009 765.6, filed Dec. 12, 2011, the entire disclosure of which is likewise incorporated herein by reference.

FIELD OF THE INVENTION

The present invention relates to a process for the preparation of (1r,4r)-6'-fluoro-N,N-dimethyl-4-phenyl-4',9'-dihydro-3'H-spiro[cyclohexane-1,1'-pyrano[3,4b]indol]-4-amine and (1r,4r)-6'-fluoro-N-methyl-4-phenyl-4',9'-dihydro-3'H-spiro[cyclohexane-1,1'-pyrano[3,4b]-indol]-4-amine or physiologically acceptable acid addition salts thereof.

BACKGROUND OF THE INVENTION

A class of active ingredients having excellent analgesic effectiveness are substituted spirocyclic cyclohexane compounds which are inter alia known from WO 2004/043967 and WO 2008/040481.

Two particular compounds that are of great interest for use in the treatment of pain such as acute, visceral, neuropathic, cancer and chronic pain are (1r,4r)-6'-fluoro-N,N-dimethyl-4-phenyl-4',9'-dihydro-3'H-spiro[cyclohexane-1,1'-pyrano[3,4b]indol]-4-amine (in the following also referred to as (1r,4r)-1) and (1r,4r)-6'-fluoro-N-methyl-4-phenyl-4',9'-dihydro-3'H-spiro[cyclohexane-1,1'-pyrano[3,4b]indol]-4-amine (in the following also referred to as (1r,4r)-2).

Substituted spirocyclic cyclohexane compounds such as (1r,4r)-1 and (1r,4r)-2 are conventionally prepared via a multi-step synthesis including an oxa-Pictet-Spengler reaction as one of the key steps as e.g. disclosed by WO 2004/043967.

The processes for the preparation of compounds (1r,4r)-1 and (1r,4r)-2 or physiologically acceptable acid addition salts thereof that are known so far are, however, not satisfactory in every respect and there is a demand for advantageous processes for the preparation of these compounds.

In particular, there is a demand for an alternative process that allows for controlling the diastereoselectivity of said process in a targeted manner, i.e. that allows for preparing (1r,4r)-1 and (1r,4r)-2 or physiologically acceptable acid addition salts thereof in pure diastereomeric form and, thus, suppressing at least partially the formation of undesired diastereomers.

SUMMARY OF THE INVENTION

It is therefore an object of the present invention to provide an alternative process which allows for the preparation of a compound according to formula (I) as depicted below, i.e. of compounds (1r,4r)-1 and (1r,4r)-2, optionally in the form of a physiologically acceptable acid addition salt thereof. A further object of the present invention is to provide such a process that has advantages over conventional processes for the preparation of a compound according to formula (I), in particular with respect to influencing the stereoselectivity such as the diastereoselectivity of the process in a targeted manner and at least partially suppressing the formation of undesired side-products and/or undesired diastereomers, and further with respect to employing environmentally acceptable conditions especially in view of a large-scale synthesis of (1r,4r)-1 and (1r,4r)-2 in multigram quantities.

This object has been achieved by the subject-matter of the patent claims, i.e. by a process for the preparation of a compound according to formula (I), optionally in the form of a physiologically acceptable acid addition salt thereof,

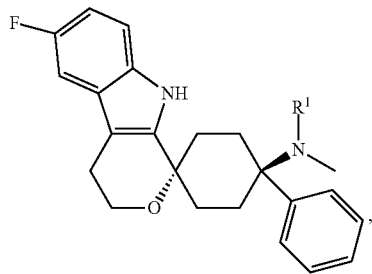

(I)

wherein $R^1$ represents H or $CH_3$,
comprising a step (a) of reacting a compound according to formula (a-1) with a compound according to formula (a-2), in each case optionally in the form of an acid addition salt such as in the form of a corresponding hydrochloride salt, in the presence of at least one mono- or diprotic acid as promoting agent,

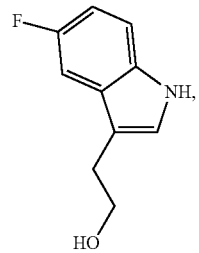

(a-1)

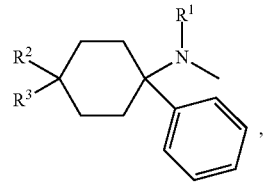

(a-2)

wherein radicals $R^2$ and $R^3$ of the compound according to formula (a-2) together denote =O, or together with the carbon atom connecting them form a cyclic moiety selected from the group consisting of

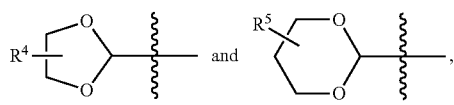

wherein $R^4$ and $R^5$ independently of one another represent in each case 0, 1, 2, 3 or 4 substituents selected from the group consisting of H and $CH_3$, in at least one carboxylic acid as reaction medium to form a compound according to formula (I), wherein $R^1$ has the above defined meaning.

It has been surprisingly found that the inventive process allows for the preparation of (1r,4r)-1 and (1r,4r)-2 in pure diastereomeric forms in at least one carboxylic acid such as acetic acid as reaction medium, i.e. allows for employing environmentally acceptable conditions especially in view of a large-scale synthesis of ((1r,4r)-1) and ((1r,4r)-2) in multi-gram quantities. Thus, the inventive process allows for sparing the use of solvents such as halogenated solvents, e.g. dichloromethane, which are assessed to be at least environmentally critical. Further, when employing at least one carboxylic acid as reaction medium in step (a) of the inventive process, it has been found that said reaction medium may be employed in a smaller amount by volume in comparison to employing a halogenated solvent such as dichloromethane in step (a), i.e. a high dilution as in the case of a halogenated solvent as reaction medium is not necessary for step (a) of the inventive process to take place, which additionally demonstrates the environmental friendliness of the inventive process. Further, due to the lower dilution, the reactor size, wherein the inventive process is performed, can be reduced significantly due to the lower dilution making the inventive process more cost-efficient.

DETAILED DESCRIPTION

The compound according to general formula (I), wherein $R^1$ denotes $CH_3$, i.e. compound (1r,4r)-1, can systematically be referred to as (1r,4r)-6'-fluoro-N,N-dimethyl-4-phenyl-4',9'-dihydro-3'H-spiro[cyclohexane-1,1'-pyrano[3,4b]indol]-4-amine or as "1,1-(3-dimethylamino-3-phenylpentamethylene)-6-fluoro-1,3,4,9-tetrahydropyrano[3,4-b]indole (trans)".

The compound according to general formula (I), wherein $R^1$ denotes H, i.e. compound (1r,4r)-2, can systematically be referred to as (1r,4r)-6'-fluoro-N-methyl-4-phenyl-4',9'-dihydro-3'H-spiro[cyclohexane-1,1'-pyrano[3,4b]indol]-4-amine or as "1,1-(3-methylamino-3-phenylpentamethylene)-6-fluoro-1,3,4,9-tetrahydropyrano[3,4-b]indole (trans)".

The compound according to general formula (I) may be present as the free base. The definition of the free base of the compound according to general formula (I) as used herein includes solvates, in particular hydrates, amorphous, co-crystals and crystalline forms, preferably includes solvates, in particular hydrates, co-crystals and crystalline forms. For the purpose of the specification, "free base" means that the compound according to general formula (I) is not present in form of a salt, particularly not in form of an acid addition salt. The most basic functional group of the compound according to general formula (I) is its N,N-dimethylamino moiety, which thus according to the invention in the form of a "free base" is neither protonated nor quaternized. In other words, the free electron pair of the nitrogen atom of the N,N-dimethylamino moiety is present as a Lewis base. Methods to determine whether a chemical substance is present as the free base or as a salt, in the form of a solvate, in a co-crystalline or crystalline form are known to the skilled artisan such as $^{14}N$ or $^{15}N$ solid state NMR, x-ray diffraction, IR, DSC, TGA, Raman, XPS. $^1H$-NMR recorded in solution may also be used to consider the presence of protonation.

The compound according to general formula (I) may, however, also be present in the form of a physiologically acceptable acid addition salt thereof. The term "physiologically acceptable acid addition salt" comprises in the sense of this invention a salt of at least one compound according to formula (I) and at least one physiologically acceptable acid, preferably in any stoichiometric ratio of the compound according to general formula (I) and the physiologically acceptable acid. The physiologically acid addition salt is in solid form, in particular in a crystalline form, co-crystalline form and/or amorphous form. The physiologically acid addition salt may also include at least one solvent and therefore may also be in the form of a solvate. Physiologically acceptable acids in the sense of this invention are inorganic or organic acids which are physiologically compatible—in particular when used in human beings and/or other mammals. Examples of physiologically acceptable acids are: hydrochloric acid, hydrobromic acid, sulfuric acid, methanesulfonic acid, trifluoromethane sulfonic acid, benzenesulfonic acid, p-toluenesulfonic acid, carbonic acid, formic acid, acetic acid, propionic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulfonic acid, nicotinic acid, 2, 3 or 4-aminobenzoic acid, 2,4,6-trimethylbenzoic acid, α-lipoic acid, acetyl glycine, hippuric acid, and aspartic acid. Trifluoromethane sulfonic acid, sulfuric acid and hydrochloric acid are preferred. Particularly preferred are sulfuric acid and hydrochloric acid, most preferred is sulfuric acid.

Within the scope of the present invention, the symbol

used in the formulae or part structures denotes a link of a corresponding residue to the respective superordinate general structure.

In a preferred embodiment according to the present invention the compound according to formula (I) is

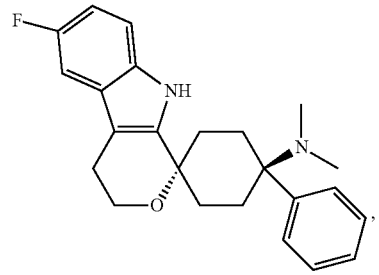 [SMILES: CN(C)[C@]1(c2ccccc2)CC[C@]2(CC1)OCCc1c3cc(F)ccc3[nH]c12]

namely (1r,4r)-6'-fluoro-N,N-dimethyl-4-phenyl-4',9'-dihydro-3'H-spiro[cyclohexane-1,1'-pyrano[3,4b]indol]-4-amine, or is

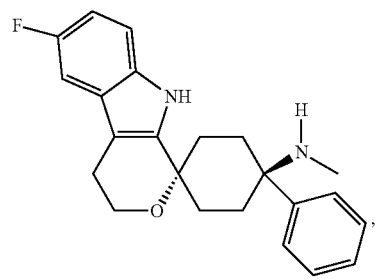

namely (1r,4r)-6'-fluoro-N-methyl-4-phenyl-4',9'-dihydro-3'H-spiro[cyclohexane-1,1'-pyrano-[3,4b]indol]-4-amine,
in each case optionally in the form of a physiologically acceptable acid addition salt thereof.

Particularly preferred is a process for the preparation of a compound according to formula (I), wherein $R^1$ is $CH_3$, i.e. for the preparation of 1r,4r-6'-fluoro-N,N-dimethyl-4-phenyl-4',9'-dihydro-3'H-spiro[cyclohexane-1,1'-pyrano[3,4b]indol]-4-amine, optionally in the form of a physiologically acceptable acid addition salt thereof.

In a further preferred embodiment according to the present invention, in compound (a-2), which is employed in step (a), radicals $R^2$ and $R^3$ of the compound according to formula (a-2) together denote =O, or together with the carbon atom connecting them form the cyclic moiety

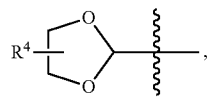

wherein $R^4$ represents 0, 1, 2, 3 or 4, preferably 0, 1 or 2, substituents selected from the group consisting of H and $CH_3$. Still more preferably, $R^4$ denotes H, i.e. $R^4$ is not present.

Preferably, in compound (a-2), which is employed in step (a), radicals $R^2$ and $R^3$ of the compound according to formula (a-2) together denote =O, or together with the carbon atom connecting them form the cyclic moiety

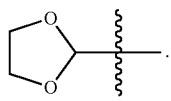

More preferably, in compound (a-2), which is employed in step (a), radicals $R^2$ and $R^3$ of the compound according to formula (a-2) together denote =O.

Reaction step (a) according to the present invention is an Oxa-Pictet-Spengler reaction which is e.g. known from S.-Y. Chou et al., Heterocycles 2003, 60, 1095 and M. Zott et al., Tetrahedron: Asymmetry 1993, 4, 2307.

The reaction of the compound according to formula (a-1) with the compound according to formula (a-2) in step (a) of the process according to the present invention takes place in at least one carboxylic acid as reaction medium. The reaction medium preferably serves as solvent for the starting material employed, i.e. for the compounds according to formulae (a-1) and (a-2), preferably also as a solvent for the promoting agent employed.

Any suitable carboxylic acid can serve as reaction medium in step (a) according to the present invention. Preferably, the carboxylic acid employed as reaction medium in step (a) according to the present invention is in liquid form at room temperature. Room temperature in the sense of the present invention is a temperature of 23° C.±7° C.

In another preferred embodiment of the present invention, the carboxylic acid employed as reaction medium in step (a) is selected from the group consisting of formic acid, acetic acid, trifluoroacetic acid, propionic acid, lactic acid, 3-hydroxypropionic acid, butyric acid, isobutyric acid, acrylic acid and methacrylic acid or mixtures thereof. Preferably, the carboxylic acid employed as reaction medium in step (a) is selected from the group consisting of formic acid, acetic acid, trifluoroacetic acid, and propionic acid or mixtures thereof. Particularly preferred are acetic acid and propionic acid. Most preferred is acetic acid.

In a particularly preferred embodiment of the present invention, the carboxylic acid employed as reaction medium in step (a) is acetic acid.

In another particularly preferred embodiment of the present invention, the carboxylic acid employed as reaction medium in step (a) is propionic acid.

Preferably, the carboxylic acid as reaction medium is employed in step (a) in an amount by weight that is in the range of from 5 to 60 times higher than the total amount of starting material according to formula (a-2) by weight. For example, in case 400 mg of the compound according to formula (a-2) is employed, the carboxylic acid as reaction medium is employed in an amount by weight, that is in the range of from 2 g to 24 g. More preferably, the carboxylic acid as reaction medium is employed in step (a) in an amount by weight that is in the range of from 7 to 50 times, even more preferably 10 to 45 times, still more preferably 12 to 40 times, in particular 15 to 35 times, and most preferred 20 to 30 times higher than the total amount of starting material according to formula (a-2) by weight.

The reaction of a compound according to formula (a-1) with a compound according to formula (a-2) in step (a) of the process according to the present invention takes place in the presence of at least one mono- or diprotic acid as promoting agent.

Preferably, the promoting agent employed in step (a) according to the inventive process is soluble, preferably soluble at room temperature, in the reaction medium employed in step (a).

Preferably, the promoting agent is at least one mono- or diprotic acid selected from the group consisting of inorganic acids and sulfonic acids. Most preferred are inorganic acids.

Suitable sulfonic acids which can be employed as promoting agent in step (a) of the inventive process are e.g. selected from the group consisting of methanesulfonic acid, trifluoromethane sulphonic acid, p-toluenesulfonic acid, and hexane-1-sulfonic acid, preferably selected from the group consisting of methanesulfonic acid and trifluoromethane sulfonic acid. The most preferred sulfonic acid is trifluoromethane sulfonic acid. Sulfonic acids can in particular be employed for the preparation of a compound according to formula (I), wherein $R^1$ is $CH_3$.

Suitable inorganic acids which can be employed as promoting agent in step (a) of the inventive process are e.g. selected from the group consisting of hydrochloric acid, hydrobromic acid, sulfuric acid, hydrogen sulfuric acid, hydrogen fluoride, hydrogen iodide, nitric acid, and sulfurous acid, preferably selected from the group consisting of hydrochloric acid, hydrobromic acid and sulfuric acid, more preferably selected from the group consisting of hydrochloric acid and sulfuric acid.

In a preferred embodiment of the present invention, the mono- or diprotic acid employed as promoting agent in step (a) is selected from the group consisting of hydrochloric acid, hydrobromic acid, sulfuric acid, and trifluoromethane sulfonic acid, preferably selected from the group consisting of hydrochloric acid, sulfuric acid, and trifluoromethane sulfonic acid.

In another preferred embodiment of the present invention at least one sulfonic acid or at least one diprotic acid is employed as promoting agent in step (a) for the preparation of a compound according to formula (I), wherein $R^1$ is $CH_3$.

In a preferred embodiment of the present invention the promoting agent is at least one monoprotic such as hydrochloric acid or trifluoromethane sulfonic acid or at least one diprotic acid such as sulfuric acid, in particular for the preparation of a compound according to formula (I), wherein $R^1$ is H.

In yet another preferred embodiment of the present invention the promoting agent is at least one diprotic acid such as sulfuric acid, in particular for the preparation of a compound according to formula (I), wherein $R^1$ is $CH_3$.

In still another preferred embodiment of the present invention the promoting agent is at least one monoprotic acid such as trifluoromethane sulfonic acid or at least one diprotic acid such as sulfuric acid, in particular for the preparation of a compound according to formula (I), wherein $R^1$ is $CH_3$. Accordingly, particularly preferred mono- or diprotic acids to be employed as promoting agent in step (a) for the preparation of a compound according to formula (I), wherein $R^1$ is $CH_3$, are selected from the group consisting of sulfuric acid and trifluoromethane sulfonic acid, preferably when acetic acid is employed as reaction medium.

In a particularly preferred embodiment of the present invention, the mono- or diprotic acid employed as promoting agent in step (a) for the preparation of a compound according to formula (I) is sulfuric acid, in particular for the preparation of a compound according to formula (I), wherein $R^1$ is $CH_3$.

In another particularly preferred embodiment of the present invention, the mono- or diprotic acid employed as promoting agent in step (a) for the preparation of a compound according to formula (I) is trifluoromethane sulfonic acid, in particular for the preparation of a compound according to formula (I), wherein $R^1$ is $CH_3$.

Particularly preferred mono- or diprotic acids to be employed as promoting agent in step (a) for the preparation of a compound according to formula (I), wherein $R^1$ is H, are selected from the group consisting of hydrochloric acid, sulfuric acid and trifluoromethane sulfonic acid.

In yet another particularly preferred embodiment of the present invention, the mono- or diprotic acid employed as promoting agent in step (a) for the preparation of a compound according to formula (I) is hydrochloric acid, in particular for the preparation of a compound according to formula (I), wherein $R^1$ is H.

Particularly preferred is also an inventive process, wherein radical $R^1$ of the compound according to formula (I) represents H and the promoting agent employed in step (a) is selected from the group consisting of hydrochloric acid, sulfuric acid and trifluoromethane sulfonic acid, preferably is hydrochloric acid, preferably when acetic acid is employed as reaction medium.

It has been surprisingly found that by the inventive process comprising step (a) the stereoselectivity, in particular the diastereoselectivity, of the product formation can be influenced in a targeted manner by choice of the reaction conditions, in particular by choice of the reaction medium and the promoting agent. In particular, it has been surprisingly found that by the inventive process comprising step (a) the desired diastereomer (1r,4r)-2 or a physiologically acceptable acid addition salt thereof having a (r,r)-configuration is exclusively formed, while the formation of the undesired diastereomer having a (s,s)-configuration, i.e. (1s,4s)-2 is suppressed, thus sparing elaborate purification or resolution steps to separate these diastereoisomers and sparing the employment of costly chiral reagents, catalysts and/or ligands. Furthermore, it has been found that by the inventive process comprising step (a) the desired diastereomer (1r,4r)-1 or a physiologically acceptable acid addition salt thereof having a (r,r)-configuration is exclusively formed, while the formation of the undesired diastereomer having a (s,s)-configuration, i.e. (1s,4s)-1 is suppressed when employing a diprotic acid or a monoprotic sulfonic acid as promoting agent, thus sparing elaborate purification or resolution steps to separate these diastereoisomers and sparing the employment of costly chiral reagents, catalysts and/or ligands (cf. Table, Examples and Comparative examples).

Preferably, the mono- or diprotic acid as promoting agent is employed in step (a) in an amount that is in the range of from 1.05 to 2.00 equivalents, preferably of from 1.10 to 1.90 equivalents, more preferably of from 1.10 to 1.70 equivalents, even more preferably of from 1.10 to 1.50 equivalents, still more preferably of from 1.10 to 1.40 equivalents, in particular of from 1.10 to 1.30 equivalents, in each case with respect to the molar amount of either the compound according to formula (a-1) or the compound according to formula (a-2).

The reaction time of step (a) can vary in dependence on various parameters, such as, for example, temperature, stoichiometry, nature of the compound to be reacted such as nature of compound (a-2), nature of the reaction medium or the properties of the promoting agent, and can be determined for the process in question by the person skilled in the art using preliminary tests. Preferably, the reaction time for performing step (a) does not exceed 24 h, more preferably does not exceed 18 h. Even more preferably, the reaction time is in the range of from 1 h to 20 h, still more preferably is in the range of from 2 h to 18, in particular is in the range of from 3 h to 16 h, most preferred is in the range of from 4 h to 10 h.

Preferably, stirring of the reaction mixture is performed in step (a).

The reaction temperature at which step (a) is performed can vary in dependence on various parameters, such as, for example, reaction time, stoichiometry, nature of the compound to be reacted such as nature of compound (a-2), nature of the reaction medium or the properties of the promoting agent, and can be determined for the process in question by the person skilled in the art using preliminary tests. Preferably, the reaction temperature at which step (a) of the inventive process is performed, is in the range of from 20° C. to 100° C., more preferably is in the range of from 30° C. to 90° C., even more preferably is in the range of from 40° C. to 80° C., still more preferably in the range of from 40° C. to 60° C. In another preferred embodiment of the present invention, the reaction temperature at which step (a) of the inventive process is performed is at least 30° C., preferably at least 40° C., more preferably at least 50° C.

In a particularly preferred embodiment of the present invention
    the at least one mono- or diprotic acid as promoting agent employed in step (a) is sulfuric acid or hydrochloric acid or trifluoromethane sulfonic acid, preferably is sulfuric acid or trifluoromethane sulfonic acid for the preparation of a compound according to formula (I), wherein $R^1$ is $CH_3$, or hydrochloric acid for the preparation of a compound according to formula (I), wherein $R^1$ is H, more preferably is sulfuric acid for the preparation of a compound according to formula (I), wherein $R^1$ is $CH_3$, preferably in an amount that is in the range of from 1.10 to 1.30 equivalents with respect to the molar amount of either the compound according to formula (a-1) or the compound according to formula (a-2),
    the at least one carboxylic acid as reaction medium employed in step (a) is acetic acid or propionic acid, preferably in an amount by weight that is in the range of from 5 to 60 times higher than the total amount of starting material according to formula (a-2) by weight.

In a very particularly preferred embodiment of the present invention the at least one mono- or diprotic acid as promoting agent employed in step (a) is sulfuric acid or hydrochloric acid or trifluoromethane sulfonic acid, preferably is sulfuric acid or trifluoromethane sulfonic acid for the preparation of a compound according to formula (I), wherein $R^1$ is $CH_3$, or hydrochloric acid for the preparation of a compound according to formula (I), wherein $R^1$ is H, more preferably is sulfuric acid for the preparation of a compound according to formula (I), wherein $R^1$ is $CH_3$, preferably in an amount that is in the range of from 1.10 to 1.30 equivalents with respect to the molar amount of either the compound according to formula (a-1) or the compound according to formula (a-2), the at least one carboxylic acid as reaction medium employed in step (a) is acetic acid or propionic acid, preferably in an amount by weight that is in the range of from 5 to 60 times higher than the total amount of starting material according to formula (a-2) by weight, the reaction temperature at which step (a) is performed is in the range of from 40° C. to 80° C., preferably in the range of from 40° C. to 60° C., and the reaction time of step (a) is in the range of from 3 h to 16 h.

Preferably, the compound according to formula (I) is obtained from step (a) in form of an acid addition salt of a compound according to formula (I) and the promoting agent. Preferably, said acid addition salt precipitates from the reaction mixture in step (a), i.e. the compound according to general formula (I) precipitates in the form of an acid addition salt from the reaction mixture during the performance of step (a) and can be thus obtained from step (a) as a precipitate, preferably by filtration of the reaction mixture, i.e. by filtering off the precipitate. Thus, preferably, the inventive process further comprises a step (a') of filtering off the acid addition salt obtained from step (a). The term "acid addition salt" in this respect comprises in the sense of this invention a salt of at least one, preferably one, compound according to formula (I) and at least one, preferably one, promoting agent, i.e. an mono- or diprotic acid employed as promoting agent, preferably in any stoichiometric ratio of the compound according to general formula (I) and the promoting agent. In case the promoting agent is a physiologically acceptable acid, the acid addition salt formed and obtained is a physiologically acceptable acid addition salt. The acid addition salt is in solid form, in particular in a crystalline form, co-crystalline form and/or amorphous form or in a multi-component complex form, i.e. a mixture thereof. The acid addition salt may also include at least one solvent molecule such as acetic acid or propionic acid or DMSO, and therefore may also be in the form of a solvate.

The acid addition salt obtained in this manner from step (a) is in solid form, in particular in a crystalline form, co-crystalline form and/or amorphous form, optionally in each case in a solvated form or as an ansolvate.

In case, hydrochloric acid is employed as promoting agent in step (a) of the inventive process, the compound according to formula (I), preferably wherein $R^1$ is H, is preferably obtained from step (a) in form of an acid addition salt of a compound according to formula (I) and hydrochloric acid, more preferably in form of (1r,4r)-6'-fluoro-N,N-dimethyl-4-phenyl-4',9'-dihydro-3'H-spiro[cyclohexane-1,1'-pyrano[3,4b]indol]-4-amine hydrochloride or (1r,4r)-6'-fluoro-N-methyl-4-phenyl-4',9'-dihydro-3'H-spiro[cyclohexane-1,1'-pyrano[3,4b]indol]-4-amine hydrochloride.

In case, sulfuric acid is employed as promoting agent in step (a) of the inventive process, the compound according to formula (I) is preferably obtained from step (a) in form of an acid addition salt of a compound according to formula (I) and sulfuric acid in any stoichiometric ratio of the compound according to general formula (I) and sulfuric acid, more preferably in form of the corresponding sulfate salt, i.e. in the form of (1r,4r)-6'-fluoro-N,N-dimethyl-4-phenyl-4',9'-dihydro-3'H-spiro[cyclohexane-1,1'-pyrano[3,4b]indol]-4-amine sulfate or (1r,4r)-6'-fluoro-N-methyl-4-phenyl-4',9'-dihydro-3'H-spiro[cyclohexane-1,1'-pyrano[3,4b]indol]-4-amine sulfate, and/or in form of the corresponding hemi-sulfate salt, i.e. in the form of (1r,4r)-6'-fluoro-N,N-dimethyl-4-phenyl-4',9'-dihydro-3'H-spiro[cyclohexane-1,1'-pyrano[3,4b]indol]-4-amine hemi-sulfate or (1r,4r)-6'-fluoro-N-methyl-4-phenyl-4',9'-dihydro-3'H-spiro[cyclohexane-1,1'-pyrano[3,4b]indol]-4-amine hemi-sulfate, even more preferably in form of the corresponding sulfate salt, i.e. in the form of (1r,4r)-6'-fluoro-N,N-dimethyl-4-phenyl-4',9'-dihydro-3'H-spiro[cyclohexane-1,1'-pyrano[3,4b]indol]-4-amine sulfate or (1r,4r)-6'-fluoro-N-methyl-4-phenyl-4',9'-dihydro-3'H-spiro[cyclohexane-1,1'-pyrano[3,4b]indol]-4-amine sulfate.

For the purpose of the specification, "sulfate" in this respect preferably means that the compound according to general formula (I) is present in the acid addition salt in a mono-protonated, mono-cationic form together with a hydrogen sulfate anion ($HSO_4^-$) as counter-ion in a stoichiometric ratio of (1.0±0.2):1.0, even more preferably in a stoichiometric ratio of (1.0±0.1):1.0, in particular in a stoichiometric ratio of 1.0:1.0.

For the purpose of the specification, "hemi-sulfate" in this respect preferably means that the compound according to general formula (I) is present in the acid addition salt in a mono-protonated, mono-cationic form together with a sulfate dianion ($SO_4^{2-}$) as counter-ion in a stoichiometric ratio of (2.0±0.2):1.0, even more preferably in a stoichiometric ratio of (2.0±0.1):1.0, in particular in a stoichiometric ratio of 2.0:1.0.

In case, trifluoromethane sulfonic acid is employed as promoting agent in step (a) of the inventive process, the compound according to formula (I) is preferably obtained from step (a) in the form of an acid addition salt of a compound according to formula (I) and trifluoromethane sulfonic acid, more preferably in form of (1r,4r)-6'-fluoro-N,N-dimethyl-4-phenyl-4',9'-dihydro-3'H-spiro[cyclohexane-1,1'-pyrano[3,4b]indol]-4-amine trifluoromethane sulfonate or (1r,4r)-6'-fluoro-N-methyl-4-phenyl-4',9'-dihydro-3'H-spiro[cyclohexane-1,1'-pyrano[3,4b]indol]-4-amine trifluoromethane sulfonate.

Preferably, the compound according to formula (I) in form of an acid addition salt of a compound according to formula (I) and a promoting agent is exclusively formed in step (a) of the inventive process, in particular when $R^1$ is $CH_3$ and the promoting agent is sulfuric acid or trifluoromethane sulfonic acid or when $R^1$ is H and the promoting agent is sulfuric acid, trifluoromethane sulfonic acid or hydrochloric acid.

The acid addition salt obtained after performing step (a) can be optionally recrystallized in a manner well known to those skilled in the art, e.g. by recrystallization from a suitable solvent, or subjected to a chromatographic resolution, e.g. in order to separate undesired side-products or the undesired stereoisomer. Suitable solvents can be determined by the person skilled in the art using preliminary tests and include solvents such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; nitriles such as acetonitrile; aromatic hydrocarbons such as toluene; saturated hydrocarbons such as n-pentane, n-hexane and n-heptane; chlorinated hydrocarbons such as dichloromethane and chloroform; and also N-methyl-2-pyrrolidone, dimethyl acetamide, dimethyl formamide and dimethyl sulfoxide (DMSO); carboxylic acids such as acetic acid and propionic acid, and mixtures thereof. Particularly preferred are acetic acid, mixtures of DMSO and acetic acid, mixtures of THF and DMSO, and mixtures of acetic acid and dimethyl acetamide. Recrystallization techniques well known to those skilled in the art e.g. include first dissolving the acid addition salt obtained from step (a) in a suitable solvent, optionally heating the mixture, followed by a precipitation of said acid addition salt, preferably by addition of another medium, or followed by evaporation of the solvent employed for dissolution.

Optionally, the inventive process may further comprise a step (a") of drying the acid addition salt obtained from step (a) and/or (a'), preferably before carrying out step (b). Step (a") may take place under air, nitrogen flow or argon flow. Further step (a") may take place under vacuum, more preferably at a vacuum of 0 to 900 mbar, even more preferably at a vacuum of 1 to 500 mbar, and in particular at a vacuum of 10 to 200 mbar. In addition, step (a") may take place in a temperature range of from 0 to 60° C., preferably of from 10° C. to 50° C., more preferably of from 20 to 40° C.

The inventive process allows the preparation of a compound according to formula (I) in the form of an a physiologically acceptable acid addition salt thereof by which can be obtained from step (a), (a') and/or (a"). Further, the inventive process allows the preparation of a compound according to formula (I) in form of the free base by further converting the product obtained from step (a).

Therefore, optionally, the acid addition salt obtained from step (a), (a') and/or (a") can be converted into the free base of the compound according to general formula (I) in a step (b). Said conversion can be effected in a manner well known to those skilled in the art. The conversion according to step (b) is preferably performed in the presence of at least one base, more preferably in a reaction medium in the presence of at least one base.

In a preferred embodiment of the present invention the inventive process further comprises said step (b) of converting the obtained acid addition salt from step (a), (a') and/or (a") into the free base of the compound according to general formula (I).

The conversion according to step (b) can be performed in any suitable reaction medium. Preferably, the reaction medium is an alcohol, preferably selected from the group consisting of methanol, ethanol, n-propanol and isopropanol. Particularly preferred alcohols are methanol, ethanol and isopropanol or mixtures thereof.

Preferably, the precipitate, i.e. the acid addition salt, obtained from step (a) is washed prior to its use in step (b) with at least one solvent which serves as reaction medium in step (b), more preferably with at least one alcohol, preferably selected from the group consisting of methanol, ethanol, n-propanol and isopropanol.

Any suitable base can be employed in step (b) of the inventive process. The base is preferably soluble in the reaction medium employed, in case such a reaction medium is employed in step (b).

Suitable bases which can be employed in step (b) of the inventive process are preferably selected from the group consisting of 1,8-diazabicyclo[5.4.0]undec-7-ene (DBU), sodium hydride (NaH), potassium hydride, sodium hydroxide (NaOH), potassium hydroxide (KOH), amines, i.e. primary, secondary and tertiary amines, more preferably amines selected from the group consisting of $NH_2(C_{1-4}$-alkyl) (alkyl amines), $NH(C_{1-4}$-alkyl)$_2$ (dialkyl amines) and $N(C_{1-4}$-alkyl)$_3$ (trialkyl amines), even more preferably from amines such as diethylamine or triethylamine, sodium methanolate, potassium tert-butylate (KOtBu) and mixtures of two of any of the aforementioned bases in any mixing ratio. More preferably, the base employed in step (b) is selected from the group consisting of NaOH, KOH, and amines, preferably amines such as diethylamine and triethylamine. In particular, the base employed in step (b) is selected from the group consisting of NaOH, KOH, and amines, in particular diethyl amine. Most preferred, the base employed in step (b) is at least one amine, preferably $NH(C_{1-4}$-alkyl)$_2$ (dialkyl amine), more preferably diethyl amine.

The base employed in step (b) may be in the form of an aqueous or alcoholic solution thereof. Preferably, the base employed in step (b) is in the form of an alcoholic solution thereof.

Preferably, step (b) is performed without any addition of water, i.e. the reaction medium is a non-aqueous reaction medium and the base employed is not in the form of an aqueous solution thereof.

Preferably, the base is employed in step (b) in an amount by weight that is in the range of from 1.2 to 20 times higher than the total amount of starting material according to formula (a-2) employed in step (a) by weight. For example, in case the total amount of the starting material according to formula (a-2) by weight employed in step (a) is 200 mg, the base is employed in an amount by weight that is in the range of from 240 mg to 4 g. More preferably, the base is employed in step (b) in an amount by weight that is in the range of from 1.5 to 17 times, even more preferably 1.7 to 15 times, still more preferably 1.8 to 12 times, in particular 1.9 to 10 times, and most preferred 2.0 to 8 times higher than the total amount of starting material according to formula (a-2) by weight employed in step (a).

In a particularly preferred embodiment of the present invention, step (b) is performed
  in a reaction medium selected from the group consisting of methanol, ethanol and isopropanol or mixtures thereof, preferably in ethanol or isopropanol,
  in the presence of at least one base, preferably at least one base selected from the group consisting of alkyl amines, dialkyl amines such as diethyl amine, and trialkyl amines, preferably in the presence of an dialkyl amine such as diethyl.

The reaction time of step (b) can vary in dependence on various parameters, such as, for example, temperature, nature of the reaction medium or the properties of the base employed, and can be determined for the process in question by the person skilled in the art using preliminary tests. However, preferably, the reaction time for performing step (b) does not exceed 24 h, more preferably does not exceed 20 h. Even more preferably, the reaction time is in the range of from 30 minutes to 20 h, still more preferably is in the range of from 45 minutes to 18 h, in particular is in the range of from 1 h to 16 h.

The reaction temperature at which step (b) is performed can vary in dependence on various parameters, such as, for example, reaction time, stoichiometry, nature of the reaction medium or the properties of the base employed, and can be determined for the process in question by the person skilled in the art using preliminary tests. Preferably, the reaction temperature at which step (b) of the inventive process is performed, is in the range of from 20° C. to 100° C., more preferably is in the range of from 20° C. to 80° C., even more preferably is in the range of from 20° C. to 60° C., still more preferably is in the range of from 20° C. to 40° C. In another preferred embodiment of the present invention, step (b) is performed at room temperature.

The free base of the compound according to formula (I) obtained from step (b) can optionally be further purified in a manner well known to those skilled in the art in a recrystallization step (c), preferably by first dissolving the free base of the compound according to formula (I) obtained from step (b) in a suitable solvent followed by a precipitation of said compound, preferably by addition of another medium, or followed by evaporation of the solvent employed for dissolution. Preferably, however, in a step (c) the free base of the compound according to formula (I) obtained from step (b) is dissolved in a suitable solvent followed by a precipitation of said compound, preferably by addition of another medium.

In a preferred embodiment of the present invention the inventive process further comprises such a step (c).

Suitable solvents for dissolving the free base of the compound according to formula (I) obtained from step (b) can be determined by the person skilled in the art using preliminary tests. Conventional solvents known to persons skilled in the art may be used as solvents in a suspension of this type, in particular organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; nitriles such as acetonitrile; aromatic hydrocarbons such as toluene; chlorinated hydrocarbons such as dichloromethane and chloroform; and also N-methyl-2-pyrrolidone, dimethyl formamide and dimethyl sulfoxide (DMSO); and mixtures thereof. Preferably, the solvent employed for dissolving the free base of the compound according to formula (I) in step (c) is dimethyl sulfoxide (DMSO).

Suitable methods for evaporating off the solvent are also known to a person skilled in the art. Preferably, in step (c) of the process according to the invention, the solvent is evaporated off in air, air flow, or inert gas flow, in particular argon or nitrogen flow. However, evaporating off the solvent under vacuum, for example by means of a rotary evaporator, is also possible. Preferably, in the process according to the invention, the solvent is evaporated off at room temperature.

Preferably, however, after dissolving the free base of the compound according to formula (I) obtained from step (b) in step (c) in a suitable solvent, said compound is precipitated by addition of another medium.

Suitable methods of precipitation are known to a person skilled in the art. In the process according to the invention, step (c) may be carried out by reducing the volume of the solution obtained in the first part of step (c), i.e. of the solution obtained by dissolution of the free base of the compound according to formula (I), and/or by cooling of the solution, preferably to a temperature of at most 15° C., more preferably at most 10° C., even more preferably at most 4-8° C., in order to achieve a precipitation.

In a preferred embodiment, the second part of step (c) is carried out by the addition of a medium in which the free base of the compound of formula (I) is only poorly soluble ("anti-solvent") to the solution obtained in the first part of step (c).

Preferably, said medium employed for precipitation of the free base of the compound according to formula (I) is selected from the group consisting of alcohols, preferably alcohols selected from the group consisting of methanol, ethanol, n-propanol and isopropanol, diethyl ether, acetone, and alkyl acetates such as ethyl acetate, more preferably the medium employed for precipitation of the free base of the compound according to formula (I) is an alcohol, even more preferably isopropanol.

The amount of the medium in which the free base of the compound according to formula (I) is only poorly soluble, the precipitant or anti-solvent, is preferably selected in such a manner that upon its addition precipitation of the dissolved component begins.

In case step (c) is performed, the free base of the compound according to formula (I) obtained after performing step (b) is preferably first dissolved in a suitable solvent, preferably in DMSO, at an elevated temperature, preferably at a temperature in the range of from 50° C. to 120°, more preferably at a temperature in the range of from 60° C. to 100°, even more preferably at a temperature in the range of from 70° C. to 90°. The resulting mixture is then cooled, preferably to a temperature in the range of from −5° C. to 40°, more preferably at a temperature in the range of from 0° C. to room temperature, followed by addition of the medium employed for precipitation of the free base of the compound according to formula (I) at this temperature.

In case step (c) is performed, the free base of the compound according to formula (I) obtained from step (b) is preferably washed prior to its use in step (c) with at least one solvent which is used as solvent in step (c), more preferably with at least one alcohol, preferably selected from the group consisting of methanol, ethanol, n-propanol and isopropanol.

The reaction time of step (c) can vary in dependence on various parameters, such as, for example, temperature, nature of the reaction medium or the properties of the base employed, and can be determined for the process in question by the person skilled in the art using preliminary tests. However, preferably, the reaction time for performing step (c) does not exceed 30 h, more preferably does not exceed 24 h. Even more preferably, the reaction time is in the range of from 30 minutes to 24 h, still more preferably is in the range of from 45 minutes to 20 h, in particular is in the range of from 1 h to 16 h.

The free base of the compound according to formula (I) obtained after performing step (c) can be optionally further treated by a suitable solvent in a step (d).

In a preferred embodiment of the present invention the inventive process further comprises such a step (d).

Suitable solvents to be employed in a step (d) can be determined by the person skilled in the art using preliminary tests. Preferably, the solvent employed in step (d) is selected from the group consisting of alcohols, preferably alcohols selected from the group consisting of methanol, ethanol, n-propanol and isopropanol, diethyl ether, acetone, and alkyl acetates such as ethyl acetate. Particularly preferred are alkyl acetates, most preferred is ethyl acetate. Preferably, compound according to formula (I) obtained after performing step (c) is dissolved or suspended in said solvent, preferably at an elevated temperature, more preferably at a temperature in the range of from 30° C. to 80° C., even more preferably at a temperature in the range of from 40° C. to 70° C. Preferably, the reaction time of step (d) is in the range of from 4 h to 18 h, more preferably in the range of from 6 h to 16 h.

Steps (c) and/or (d) may be repeated in order to further purify the compound according to formula (I) obtained, if necessary.

Optionally, the compound according to formula (I) in the form of a free base as obtained after performance of step (b), (c) or (d) may be converted into a corresponding physiologically acceptable acid addition salt in a step (e) following step (b), (c) or (d). Said conversion may be effected in a manner well known to those skilled in the art. Salt formation is preferably effected in a solvent, for example, diethyl ether, diisopropyl ether, ethanol, methanol, alkyl acetates, acetone and/or 2-butanone. Moreover, trimethylchlorosilane in a protic reaction medium is also suitable for the preparation of hydrochlorides.

Preferably, stirring is performed during steps (a), (b), (c), (d) and/or (e) of the inventive process.

The steps according to the process according to the present invention can be carried out discontinuously (batchwise) or continuously, preference being given to the discontinuous procedure.

There come into consideration as the reactor for the discontinuous procedure, for example, a slurry reactor, and for the continuous procedure a fixed-bed reactor or loop reactor.

EXAMPLES

The following examples further illustrate the invention but are not to be construed as limiting its scope.
General Procedure:
Step (a)

A compound according to formula (a-1) (1 equivalent) and a compound according to formula (a-2) (1 equivalent) are dissolved in at least one carboxylic acid as reaction medium such as acetic acid or propionic acid, wherein the reaction medium is preferably employed in an amount by weight that is in the range of from 5 to 60 times higher than the total amount of starting material according to formula (a-2) by weight. The resulting mixture is heated to a temperature in the range of from 20° C. to 100° C. and at least one mono- or diprotic acid as promoting agent such as hydrochloric acid or sulfuric acid, preferably in an amount that is in the range of from 1.05 to 2.00 equivalents, with respect to the molar amount of the compound according to formula (a-1) or (a-2), is added and the resulting mixture is stirred at this temperature for a time that is in the range of from 1 h to 20 h (reaction time). During the reaction time a precipitate, i.e. an acid addition salt of a compound of formula (I) and an acid, forms, which is then filtered off and preferably washed with a solvent, preferably with an alcohol such as ethanol or isopropanol.
Step (b)

To the precipitate obtained from step (a) is added at least one base such as diethyl amine or sodium or potassium hydroxide in a reaction medium, preferably in an alcohol such as isopropanol or ethanol, wherein the base is preferably employed in step (b) in an amount by weight that is in the range of 1.2 to 20 times higher than the amount of the starting material according to formula (a-2) by weight. The resulting mixture is stirred for a time that is in the range of from 30 minutes to 20 h (reaction time) at a reaction temperature in the range of from 20° C. to 100° C., preferably at room temperature. During the reaction time a precipitate, i.e. a compound according to formula (I) in the form of a free base, forms, which is then filtered off and washed with a solvent, preferably with an alcohol, such as ethanol or isopropanol.
Step (c)

To the precipitate obtained from step (b) is added a solvent such DMSO and the resulting mixture is heated to a temperature in the range of from 50° C. to 120° until the precipitate is completely dissolved at this temperature. Then the mixture is cooled to a temperature in the range of from −5° C. to 40°, and at this temperature a further medium, preferably an alcohol such as isopropanol is added to cause a precipitation of the desired product, i.e. a compound according to formula (I) in the form of a free base in recrystallized form, which is preferably obtained after a reaction time which is in the range of from 30 minutes to 24 h.
Step (d)

The precipitate obtained from step (c) may optionally be further treated with a suitable solvent such as ethyl acetate, preferably at a temperature in the range of from 40° C. to 70° C. in a reaction time which is the range of from 6 h to 16 h.

Examples According to the Invention

Synthesis of (1r,4r)-6'-fluoro-N,N-dimethyl-4-phenyl-4',9'-dihydro-3'H-spiro[cyclohexane-1,1'-pyrano[3,4b]indol]-4-amine((1r,4r)-1)

Example 1

Sulfuric Acid as an Example of a Diprotic Acid as Promoting Agent; Acetic Acid as Reaction Medium in Step (a)

23.65 g (0.132 mol) of 2-(5-fluoro-1H-indol-3-yl)ethanol and 28.68 g (0.132 mol) of 4-(dimethylamino)-4-phenylcyclohexanone are dissolved in 717 ml of acetic acid. The mixture is warmed up to 45-50° C. under stirring. At 45-50° C. 8.44 ml (0.158 mol) of sulfuric acid are added over a period of 20-30 seconds. The resulting solid is stirred for 4-16 h at 50-60° C. The mixture is cooled to 20° C., filtered off and washed subsequently with each 72 ml of acetic acid and isopropanol. The solid, i.e. an acid addition salt of (1r,4r)-1 and sulfuric acid, is suspended in 550 ml of isopropanol and 42 ml of diethyl amine are added. The resulting suspension is stirred at room temperature for 17-20 h. The solid is filtered off and washed with 144 ml of isopropanol. 450 ml of DMSO are added to dissolve the solid at 80-87° C. Then 1200 ml of isopropanol are added and the mixture is cooled to room temperature. The resulting solid is filtered off after 3-24 h and washed with 200 ml of isopropanol. The solid is suspended in 250 ml of ethyl acetate and stirred at 55-70° C. for 10-24 h. The solid is filtered off and dried in vacuum. Yield of (1r,4r)-1: 50-60%.

Example 2

Trifluoromethane Sulfonic Acid as an Example of a Monoprotic Acid as Promoting Agent; Acetic Acid as Reaction Medium in Step (a)

4.48 g (0.025 mol) of 2-(5-fluoro-1H-indol-3-yl)ethanol and 5.43 g (0.025 mol) of 4-(dimethylamino)-4-phenylcyclohexanone are dissolved in 81 ml of acetic acid. The mixture is warmed up to 43° C. under stirring. At 45-50° C. 8.44 ml (0.158 mol) of trifluoromethane sulfonic acid are added over a period of 20-30 seconds. The resulting solid is stirred for 4-16 h at 50-60° C. The mixture is cooled to 20° C., filtered off and washed subsequently with each 7 ml of acetic acid and 27 ml of ethanol. The solid, i.e. an acid addition salt of (1r,4r)-1 and trifluoromethane sulfonic acid is suspended in 25 ml of ethanol and 4 ml of diethylamine are added. The resulting suspension is stirred at room temperature for 17-20 h. The solid is filtered off and washed with 25 ml of ethanol. 120 ml of DMSO are added to dissolve the solid at 80-87° C. Then 135 ml of isopropanol are added and the mixture is cooled to 5° C. The resulting solid is filtered off after 1 h and washed with 30 ml of isopropanol. The solid is filtered off and dried in vacuum. Yield of (1r,4r)-1: 27% (99.9% diastereomeric purity).

Synthesis of (1r,4r)-6'-fluoro-N-methyl-4-phenyl-4', 9'-dihydro-3'H-spiro[cyclohexane-1,1'-pyrano[3,4b] indol]-4-amine((1r,4r)-2)

Example 3

Hydrochloric Acid as an Example of a Monoprotic Acid as Promoting Agent; Acetic Acid as Reaction Medium in Step (a)

6.32 g (0.035 mol) of 2-(5-fluoro-1H-indol-3-yl)ethanol and 10.0 g (0.035 mol) of the hydrochloride salt of 4-(methylamino)-4-phenyl-1-(1,3-dioxolanyl)-cyclohexane are dissolved in 100 ml of acetic acid. The mixture is warmed up to 40° C. under stirring. 0.84 ml (0.071 mol) of hydrochloric acid are added. The resulting solid is stirred for 4-16 h at 40° C. The mixture is cooled to 20° C., filtered off and washed subsequently with 20 ml of acetic acid and 10 ml of isopropanol. The solid, i.e. an acid addition salt of (1r,4r)-2 and hydrochloric acid, is suspended in 30 ml of isopropanol and 6.7 ml of diethyl amine are added. The resulting suspension is stirred at room temperature for 17-20 h. The solid is filtered off and washed with 10 ml of isopropanol. 20 ml of DMSO are added to dissolve the solid at 80-87° C. Then 50 ml of isopropanol are added and the mixture is cooled to room temperature. The resulting solid is filtered off after 3-24 h and washed with 10 ml of isopropanol. The solid is suspended in 30 ml of ethyl acetate and stirred at 55-70° C. for 2-24 h. The solid is filtered off at 5-8° C., washed with 5 ml of ethyl acetate and dried in vacuum. Yield of (1r,4r)-2: 30-40%.

Comparative Examples (not Inventive)

Synthesis of (1s,4s)-6'-fluoro-N,N-dimethyl-4-phenyl-4',9'-dihydro-3'H-spiro[cyclohexane-1,1'-pyrano [3,4b]indol]-4-amine((1s,4s)-1)(undesired diastereomer)

Comparative Example 1

Sulfuric Acid as Promoting Agent; Ethanol as Reaction Medium in Step (a)

4.48 g (0.025 mol) of 2-(5-fluoro-1H-indol-3-yl)-ethanol and 5.43 g (0.025 mol) of 4-dimethylamino-4-phenylcyclohexanone are dissolved in 81 ml of ethanol. The mixture is warmed up to 45-50° C. under stirring. At 45-50° C. 3.06 g (0.031 mol) of sulfuric acid are added over a period of 20-30 seconds. The resulting solid is stirred for 1 h at 50-60° C. Intermediate DC control showed little conversion and another 1 ml of sulfuric acid is added. The mixture is stirred for 16 h at 55° C. The mixture is cooled to 20° C., filtered off and washed twice with each 7 ml of ethanol. The solid is suspended in 9 ml of ethanol and 4 ml of diethyl amine are added. The resulting suspension is stirred at room temperature for 17-20 h. The solid is filtered off and washed with 20 ml of ethanol. 120 ml of DMSO are added to dissolve the solid at 80-87° C. Then 140 ml of isopropanol are added and the mixture is cooled to room temperature. The resulting solid is filtered off after 3-24 h and washed with 35 ml of isopropanol. The solid is filtered off and dried. Analytics shows 78% of (1s,4s)-1 which is the undesired diastereoisomer. Yield of ((1s,4s)-1): 21%.

Comparative Example 2

Phosphoric Acid as an Example of a Triprotic Acid as Promoting Agent; Acetic Acid as Reaction Medium in Step (a) (According to Example 25 of WO 2004/043967)

4-dimethylamino-4-phenylcyclohexanone (217 mg, 1 mmol) and 2-(5-fluoro-1H-indol-3-yl)-ethanol (179 mg, 1 mmol) are dissolved in acetic acid (4 mL). Phosphoric acid (1 mL, 85 wt. %) is slowly added dropwise to this mixture. Stirring is performed for 16 h at RT. The batch is worked up by being diluted with water (20 mL), adjusted to pH 11 with 5M NaOH and extracted with dichloromethane (3×20 mL). The combined organic phase is dried with sodium sulfate and is evaporated. The residue (364 mg of white solid) is suspended in hot ethanol (20 mL) and is combined with a likewise hot solution of citric acid (185 mg, 0.96 mmol) in ethanol (5 mL). In this manner, the residue is completely dissolved. No precipitation is observed, even when cooling to approximately 5° C. is performed. Ethanol is removed in a rotary evaporator and, in this manner, the hemicitrate of (1s, 4s)-1 (the more highly polar diastereoisomer) is obtained in a yield of 548 mg as a white solid. Said diastereomer is the undesired diastereomer.

The experimental results of Examples 1-3 and Comparative Examples 1 and 2 are summarized in the Table as depicted below:

TABLE

| step (a) according to example/comparative example | reaction medium employed in step (a) | promoting agent employed in step (a) | product obtained |
| --- | --- | --- | --- |
| Example 1 | acetic acid | sulfuric acid | (1r,4r)-1, ("trans"), desired diastereomer according to the invention |
| Example 2 | acetic acid | trifluoromethane sulfonic acid | (1r,4r)-1, ("trans"), desired diastereomer according to the invention |
| Example 3 | acetic acid | hydrochloric acid | (1r,4r)-2, ("trans"), desired diastereomer according to the invention |

TABLE-continued

| step (a) according to example/comparative example | reaction medium employed in step (a) | promoting agent employed in step (a) | product obtained |
|---|---|---|---|
| Comparative Example 1 | ethanol | sulfuric acid | (1s,4s)-1, ("cis"), undesired diastereomer |
| Comparative Example 2 (according to example 25 of WO 2004/043967) | acetic acid | phosphoric acid | (1s,4s)-1, ("cis"), undesired diastereomer) |

As can be derived from the results of Comparative Example 1 displayed in the Table, by employing a reaction medium other than a carboxylic acid such as an alcohol in step (a) of the inventive process, a compound of formula (I) according to the present invention, e.g. compound (1r,4r)-1, cannot be obtained since only the undesired diastereomeric form (1s,4s)-1 is formed.

As can be derived from the results of Comparative Example 2 displayed in the Table, by employing a triprotic acid such as phosphoric acid instead of a mono- or diprotic acid in step (a) of the inventive process, a compound of formula (I) according to the present invention, e.g. compound (1r,4r)-1, cannot be obtained since only the undesired diastereomeric form (1s,4s)-1 is formed.

Only according to the inventive process, i.e. according to a process, wherein in step (a) at least one carboxylic acid and as a promoting agent at least one mono- or diprotic acid is employed, a compound of formula (I) according to the present invention, i.e. compound (1r,4r)-1 and (1r,4r)-2, respectively, each having the desired (r,r)-configuration, can be obtained exclusively, while the formation of the undesired (s,s)-diastereomer is suppressed, as can be derived from Examples 1-3.

Further, as can be derived from Examples 1-3, the inventive process allows for the preparation of ((1r,4r)-1) and ((1r,4r)-2) in pure diastereomeric forms in at least one carboxylic acid such as acetic acid as reaction medium, i.e. allows for employing environmentally acceptable conditions especially in view of a large-scale synthesis of ((1r,4r)-1) and ((1r,4r)-2) in multigram quantities. Thus, the inventive process allows for sparing the use of solvents such as halogenated solvents, e.g. dichloromethane, which are assessed to be at least environmentally critical. In addition, the size of the required reactor can be reduced significantly due to the lower dilution making the process more cost-efficient.

The foregoing description and examples have been set forth merely to illustrate the invention and are not intended to be limiting. Since modifications of the described embodiments proratingting the spirit and substance of the invention may occur to persons skilled in the art, the invention should be construed broadly to include all variation within the scope of the appended claims and equivalents thereof.

The invention claimed is:

1. A process for preparing a compound corresponding to formula (I)

(I)

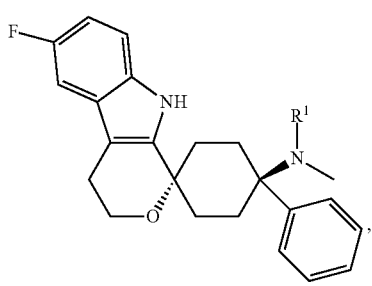

wherein $R^1$ represents H or $CH_3$, or a physiologically acceptable acid addition salt thereof, said process comprising:

(a) reacting a compound corresponding to formula (a-1) with a compound corresponding to formula (a-2), in each case optionally in the form of an acid addition salt, in the presence of at least one mono- or diprotic acid promoting agent,

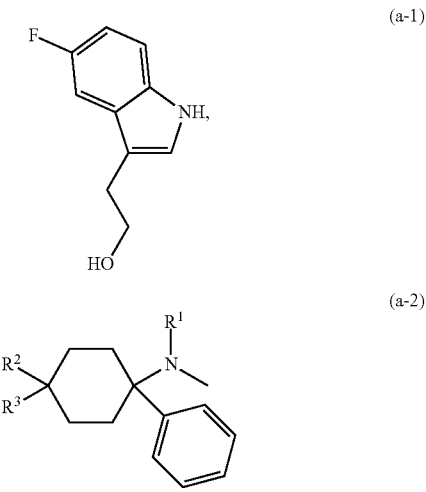

wherein $R^2$ and $R^3$ in the compound of formula (a-2) together denote =O, or together with the carbon atom connecting them form a cyclic moiety selected from the group consisting of

wherein $R^4$ and $R^5$ each independently represent 0, 1, 2, 3 or 4 substituents selected from the group consisting of H and $CH_3$, in a carboxylic acid reaction medium to form the compound of formula (I).

2. The process according to claim 1, wherein the compound of formula (I) is (1r,4r)-6'-fluoro-N,N-dimethyl-4-phenyl-4',9'-dihydro-3'H-spiro[cyclohexane-1,1'-pyrano-[3,4b]indol]-4-amine having the formula:

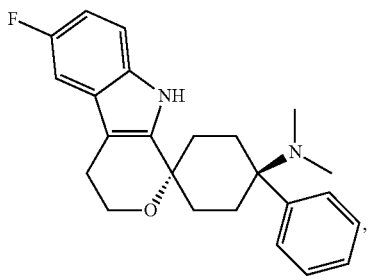 [SMILES: CN(C)[C@]1(c2ccccc2)CC[C@]2(CC1)OCCc1c3cc(F)ccc3[nH]c12]

or (1r,4r)-6'-fluoro-N-methyl-4-phenyl-4',9'-dihydro-3'H-spiro[cyclohexane-1,1'-pyrano-[3,4b]indol]-4-amine having the formula:

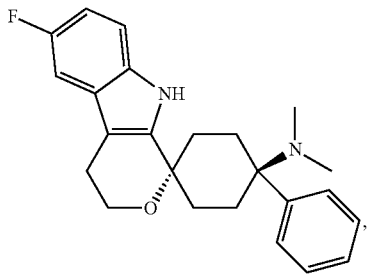 [SMILES: CN(C)[C@]1(c2ccccc2)CC[C@]2(CC1)OCCc1c3cc(F)ccc3[nH]c12]

or a physiologically acceptable acid addition salt thereof.

3. The process according to claim 1, wherein the reaction medium comprises at least one carboxylic acid selected from the group consisting of formic acid, acetic acid, trifluoroacetic acid, propionic acid, lactic acid, 3-hydroxypropionic acid, butyric acid, isobutyric acid, acrylic acid, methacrylic acid, and mixtures of two or more of the foregoing.

4. The process according claim 3, wherein the reaction medium comprises acetic acid or propionic acid or a mixture of acetic acid and propionic acid.

5. The process according to claim 1, wherein the promoting agent is soluble in the reaction medium.

6. The process according to claim 1, wherein the promoting agent is selected from the group consisting of inorganic acids and sulfonic acids.

7. The process according to claim 1, wherein the promoting agent is selected from the group consisting of methanesulfonic acid, trifluoromethane sulfonic acid, p-toluenesulfonic acid, hexane-1-sulfonic acid, hydrochloric acid, hydrobromic acid, sulfuric acid, hydrogen sulfuric acid, hydrogen fluoride, hydrogen iodide, nitric acid, and sulfurous acid.

8. The process according to claim 1, wherein the promoting agent is selected from the group consisting of hydrochloric acid, sulfuric acid, and trifluoromethane sulfonic acid.

9. The process according to claim 1, wherein the compound of formula (I) is obtained in the form of an acid addition salt of said compound of formula (I) and said promoting agent.

10. The process according to claim 1, wherein:
$R^1$ represents $CH_3$, and
the promoting agent is selected from the group consisting of sulfuric acid and trifluoromethane sulfonic acid.

11. The process according to claim 1, wherein:
$R^1$ represents H, and
the promoting agent is selected from the group consisting of hydrochloric acid, sulfuric acid and trifluoromethane sulfonic acid.

12. The process according to claim 1, further comprising:
(b) converting a compound of formula (I) obtained from step (a) in the form of an acid addition salt with the promoting agent into the corresponding free base of formula (I).

13. The process according to claim 12, wherein step (b) is carried out in a reaction medium in the presence of at least one base.

14. The process according to claim 13, wherein:
said reaction medium selected from the group consisting of methanol, ethanol, isopropanol and mixtures of two or more of the foregoing, and
said base is selected from the group consisting of alkyl amines, dialkyl amines and trialkyl amines.

15. The process according to claim 12, further comprising recrystallizing said free base of the compound of formula (I) obtained from step (b).

* * * * *